United States Patent
Matsumoto

(10) Patent No.: US 9,281,100 B2
(45) Date of Patent: Mar. 8, 2016

(54) COILED CABLE

(71) Applicant: JUNKOSHA INC., Kasama-shi, Ibaraki (JP)

(72) Inventor: Osamu Matsumoto, Mito (JP)

(73) Assignee: JUNKOSHA, INC., Kasama-Shi (JP)

(*) Notice: Subject to any disclaimer, the term of this patent is extended or adjusted under 35 U.S.C. 154(b) by 0 days.

(21) Appl. No.: 14/395,947

(22) PCT Filed: Apr. 22, 2013

(86) PCT No.: PCT/JP2013/061721
§ 371 (c)(1),
(2) Date: Oct. 21, 2014

(87) PCT Pub. No.: WO2013/161730
PCT Pub. Date: Oct. 31, 2013

(65) Prior Publication Data
US 2015/0114681 A1    Apr. 30, 2015

(30) Foreign Application Priority Data

Apr. 27, 2012 (JP) .................................. 2012-104235

(51) Int. Cl.
*H01B 7/00*   (2006.01)
*H01B 7/04*   (2006.01)
*A61N 1/05*   (2006.01)
*H01B 3/30*   (2006.01)

(52) U.S. Cl.
CPC ....... *H01B 7/048* (2013.01); *A61N 1/05* (2013.01); *H01B 3/30* (2013.01); *A61N 1/056* (2013.01)

(58) Field of Classification Search
CPC .............. H01B 3/00; H01B 7/00; H01B 9/00
USPC ............ 174/102 R, 103, 105 R, 108, 110 R, 174/113 R, 112
See application file for complete search history.

(56) References Cited

U.S. PATENT DOCUMENTS

| 4,861,945 | A | | 8/1989 | Buck et al. | |
|---|---|---|---|---|---|
| 5,372,138 | A | * | 12/1994 | Crowley | A61B 5/416 600/463 |
| 5,439,713 | A | * | 8/1995 | Yamaoka | C23C 2/26 427/406 |
| 5,796,044 | A | | 8/1998 | Cobian et al. | |
| 6,004,269 | A | * | 12/1999 | Crowley | A61B 8/445 600/374 |

(Continued)

FOREIGN PATENT DOCUMENTS

| JP | 08-138449 | 5/1996 |
|---|---|---|
| JP | 09-007425 | 1/1997 |

(Continued)

OTHER PUBLICATIONS

International Search Report, Date of Mailing: Jul. 2, 2013.

*Primary Examiner* — William H Mayo, III
(74) *Attorney, Agent, or Firm* — Rankin, Hill & Clark LLP

(57) ABSTRACT

A coiled cable (10) has a conductor coil (12) formed into a coil shape having a coil average diameter (D) by winding four conductor base lines (21-24) with a diameter (d) to each of which an insulating coating layer (42) is applied. The conductor coil (12) is set to have an spring index (D/d) represented by 2≤D/d≤4, and each of the conductor base lines (21-24) is configured by twisting a plurality of materials that have φ0.008 to φ0.05 and that are made of tough pitch copper, oxygen-free copper, or copper alloy wire.

9 Claims, 5 Drawing Sheets

(56) References Cited

U.S. PATENT DOCUMENTS

| | | |
|---|---|---|
| 6,289,250 B1 | 9/2001 | Tsuboi et al. |
| 6,580,949 B1 | 6/2003 | Tsuboi et al. |
| 2009/0149933 A1* | 6/2009 | Ameri .................. A61N 1/05 607/119 |
| 2012/0053665 A1* | 3/2012 | Stolz .................. A61N 1/0558 607/118 |

FOREIGN PATENT DOCUMENTS

| | | |
|---|---|---|
| JP | 11-333000 | 12/1999 |
| JP | 2001-029480 | 2/2001 |
| JP | 2010-273912 | 12/2010 |
| JP | 2011-504405 | 2/2011 |
| JP | 2012-073213 | 4/2012 |
| WO | 2010/065049 | 6/2010 |
| WO | 2010/151376 | 12/2010 |

\* cited by examiner

10B

10C

COILED CABLE

TECHNICAL FIELD

The present invention relates to a coiled electric cable which is used for an implant in a medical field or used in a narrow space in a field of a small-sized robot.

BACKGROUND ART

For example, an electric cable used for a pacemaker causing heartbeats by providing periodic electric stimulation to a heart or an electric cable used for a small-sized robot assisting movement of limbs of the human body is required to be flexible in accordance with an operation of a wiring site, and to have resistance to repeated bending or bending with an extremely small curvature, so that an electric cable which is wound to have a coil shape has been used in order to satisfy such durability.

As such an existing coiled electric cable, Patent Document 1 discloses a coiled electric cable formed in a coil shape by arranging a plurality of conductor base lines in parallel. The conductor base lines are composed of: a clad structure whose outer periphery of a center material made of silver or copper is integrated with an outer material made of stainless steel or a cobalt-based alloy; and an insulation coating layer made of a fluorine resin or the like which covers the outer periphery of the clad structure. The coiled electric cable is stretchable because the plurality of the conductor base lines are arranged in parallel to form a coil shape, has low electric resistance because the center material is formed of silver or copper, and have high tensile strength because the outer material is formed of stainless steel or a cobalt-based alloy. Consequently, the durability of the coiled electric cable can be increased.

RELATED ART DOCUMENT

Patent Document

[Patent Document 1] JP-A-11-333000

SUMMARY OF INVENTION

Problems to be Solved by Invention

However, in the coiled electric cable disclosed in Patent Document 1 described above, it is necessary to set a so-called spring index (D/d) to be a large value for improving durability, so that it has been considered that the spring index (D/d) is necessary to be set to a value of 7.8 or greater for obtaining sufficient durability. For this reason, the outer diameter of a coil is required to be larger, and as a result, problems of increase in installation space, weight, and in conductor resistance, and decrease in flexibility are caused.

The present invention has been made in consideration of the above-described problems, and an object thereof is to solve the above-described problems in the coiled electric cable in the related art and to provide a coiled electric cable which has excellent durability, has a small outer diameter, is light in weight, has low conductor resistance, and has excellent flexibility.

Means for Solving the Problems

In order to achieve the object above, a coiled cable according to the present invention includes a conductor coil formed by winding 1 to 8 conductor base lines having a diameter (d), to each of which an insulation coating layer is applied, into a coil shape having a coil average diameter (D), and the conductor coil is set to have a spring index (D/d) satisfying a relationship of $2 \leq D/d \leq 4$, and the conductor base lines are configured by twisting a plurality of conductor materials having a diameter of $\phi 0.008$ to $\phi 0.05$. The conductor base lines may be electric wires which include a plurality of conductors and an insulator layer or may be coaxial cables which include an inner conductor, a dielectric layer, an outer conductor layer, and a protective coating layer. The insulation coating layer includes a fluorine resin including one or two or more materials selected from an ethylene-tetrafluoroethylene copolymer (ETFE), a tetrafluoroethylene-hexafluoropropylene copolymer (FEP), a perfluoroalkyl vinyl ether copolymer resin (PFA), and polytetrafluoroethylene (PTFE). A resin layer having a stretch property and having a shore A hardness of 90 or less is preferably provided as a covering layer which covers an inner peripheral surface or an outer peripheral surface of the conductor coil.

That is, the present inventor has found that much more excellent durability than that of coiled cables in the related art can be obtained and excellent flexibility also can be obtained, even when the spring index (D/d) of the conductor coil is in the range of 2 to 4, by configuring the above-described conductor base lines by twisting a plurality of conductor materials having a diameter of $\phi 0.008$ to $\phi 0.05$. Further, the present inventor has found that a coiled cable with low conductor resistance can be prepared by adjusting the spring index (D/d) of the conductor coil to be in the range of 2 to 4. In this manner, a coiled electric cable which has more excellent durability than the coiled cable in the related art, has a smaller outer diameter, is light in weight, has low conductor resistance, and has excellent flexibility can be obtained.

EMBODIMENTS FOR CARRYING OUT THE INVENTION

An embodiment described below is not intended to limit the invention according to the claims, and it cannot be said that all combinations of characteristics described in the embodiment are necessary for establishment of the present invention.

Figure 1:
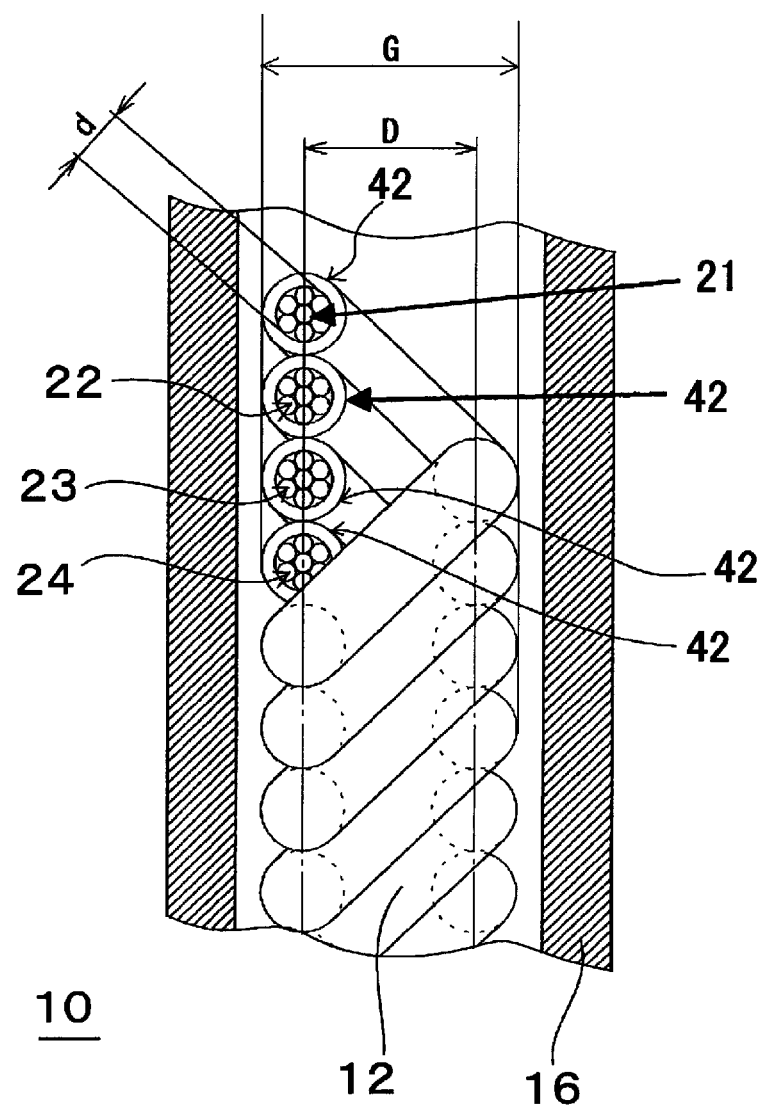
FIG. 1 is a plan view illustrating a coiled cable according to an embodiment of the present invention when seen from a direction orthogonal to the axis thereof.

FIG. 1 is a plan view illustrating a coiled cable 10 according to an embodiment of the present invention when seen from a direction orthogonal to the axis thereof. The coiled cable 10 according to the embodiment of the present invention includes a conductor coil 12 formed by winding 1 to 8 (four in the example of FIG. 1) conductor base lines 21 to 24 having a diameter (d) as element wires, to each of which an insulation coating layer 42 is applied, into a coil shape having a coil average diameter (D), and a spring index (D/d) of the conductor coil 12 is set to satisfy a relationship of 2≤D/d≤4.

Each of the conductor base lines 21 to 24 is configured by twisting a plurality of conductor materials having a diameter of φ0.008 to φ0.05, which are made of, for example, tough pitch copper, oxygen-free copper, or copper alloy wire. As described above, in the embodiment of the present invention, as illustrated in FIG. 1, d represents a diameter of each of the conductor base lines 21 to 24 as element wires from which the insulation coating layer 42 is removed, D represents an average diameter of the conductor coil 12, and D/d is a spring index of the conductor coil 12. D represents the average diameter of the conductor coil 12, and the average diameter means an average between the outer diameter and the inner diameter of a coil portion of the conductor coil 12 and corresponds to a diameter of the coil portion of the conductor coil 12 which connects the centers of respective conductor base lines 21 to 24, as is evident from FIG. 1.

Further, in the coiled cable 10, a covering layer 16 is provided such that the outer peripheral surface of the conductor coil 12 having a final outer diameter G of, for example, 0.82 mm is covered by the covering layer 16. In addition, the coiled cable 10 is used for an implant in a medical field or used in a narrow space in a field of a small-sized robot. In the medical field of the implant, the coiled cable 10 is required to have a particularly small diameter and flexibility. Moreover, each of the conductor base lines 21 to 24 may be an electric wire (a simple wire) including a plurality of conductors and an insulator layer; or a coaxial cable including an inner conductor, a dielectric layer, an outer conductor layer, and a protective coating layer.

Furthermore, the insulation coating layer 42 includes a fluorine resin including one or two or more materials among an ethylene-tetrafluoroethylene copolymer (ETFE), a tetrafluoroethylene-hexafluoropropylene copolymer (FEP), a perfluoroalkyl vinyl ether copolymer resin (PFA), and polytetrafluoroethylene (PTFE).

Furthermore, the coiled cable 10 of the present embodiment includes a resin layer having a stretch property and having a shore A hardness of 90 or less as the covering layer 16 which covers the outer peripheral surface of the conductor coil 12. Such a resin layer may be formed so as to cover the inner peripheral surface of the conductor coil 12.

In addition, in the coiled cable 10 having such a configuration, since the base material of the insulation coating layer 42 of the conductor base lines 21 to 24 is a fluorine resin, the insulation coating layer 42 is excellent in biocompatibility, wear resistance, chemical resistance, and oil resistance even though the thickness thereof is small.

Next, as Examples, coiled cables 10 having spring indices (D/d) of the above-described conductor coil which are different from one another within the range of 2≤D/d≤4 and including conductor base lines configured by twisting a plurality of tough pitch copper, oxygen-free copper, or copper alloy wire, having a diameter of φ0.008 to φ0.05, were prepared. As Comparative Examples, coiled cables 10 having spring indices (D/d) of the conductor coil outside of 2≤D/d≤4 and having a different configuration of the conductor base lines, were prepared. For the Examples and the Comparative Examples, a bending test was performed to investigate durability of the respective cables, and the test results are described below.

Here, test coiled cables used in the present test, that is, coiled cables of Examples 1 to 3 and coiled cables of Comparative Examples 1 to 3, are prepared as follows.

Example 1

Figure 2:
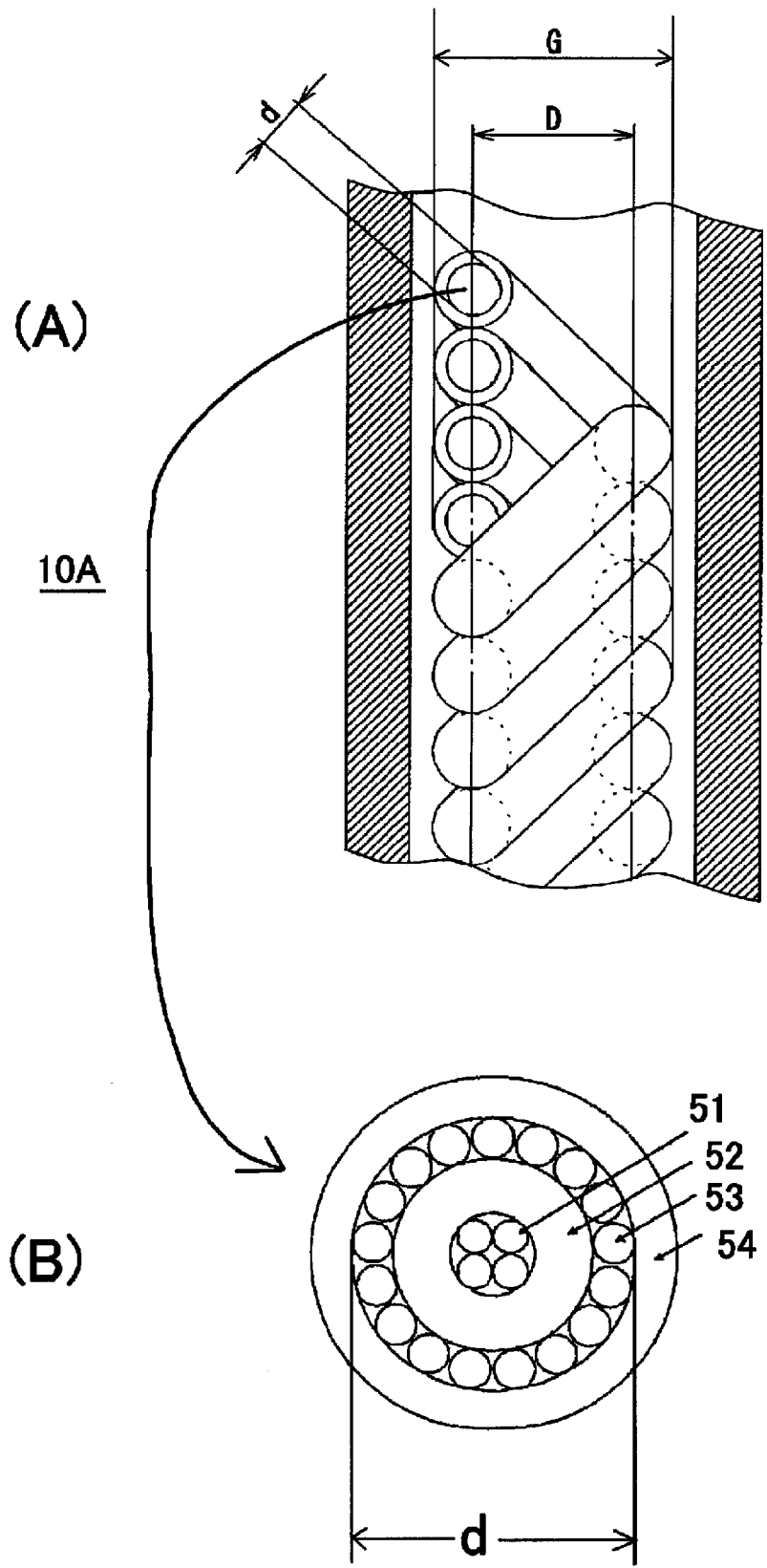
FIG. 2 include: part (A) that is a plan view illustrating Example 1 of a coiled cable according to the embodiment of the present invention when seen from the direction orthogonal to the axis thereof; and part (B) that is an enlarged view illustrating conductor base lines when seen from the axis direction.

A coiled cable 10A of Example 1 is illustrated in FIG. 2. The coiled cable 10A was a coaxial cable type of so-called AWG46, and had a dimensional structure with which a spring index (D/d) of the conductor coil of 3.59 was achieved in part (A) of FIG. 2.

In part (B) of FIG. 2, a central conductor 51 was configured by twisting four silver-plated and silver-containing copper alloy wires having an outer diameter of 0.021 mm. A dielectric layer 52 was formed by covering the central conductor Si with a PFA to have an outer diameter thereof of 0.117 mm. Further, an outer conductor layer 53 was formed by horizontally winding seventeen tin-plated and tin-containing copper alloy wires having an outer diameter of 0.025 mm which correspond to conductor element wires, and a jacket layer 54 was formed by extruding a jacket made of an PEP having a thickness of 0.0265 mm to cover the outer conductor layer 53 and to have an outer diameter of 0.22 mm. In addition, four of the above-described cables were tightly wound to have a coil shape, a heat treatment was performed thereon for heat-setting, and the final outer diameter G was φ0.82 mm.

Example 2

Figure 3A:
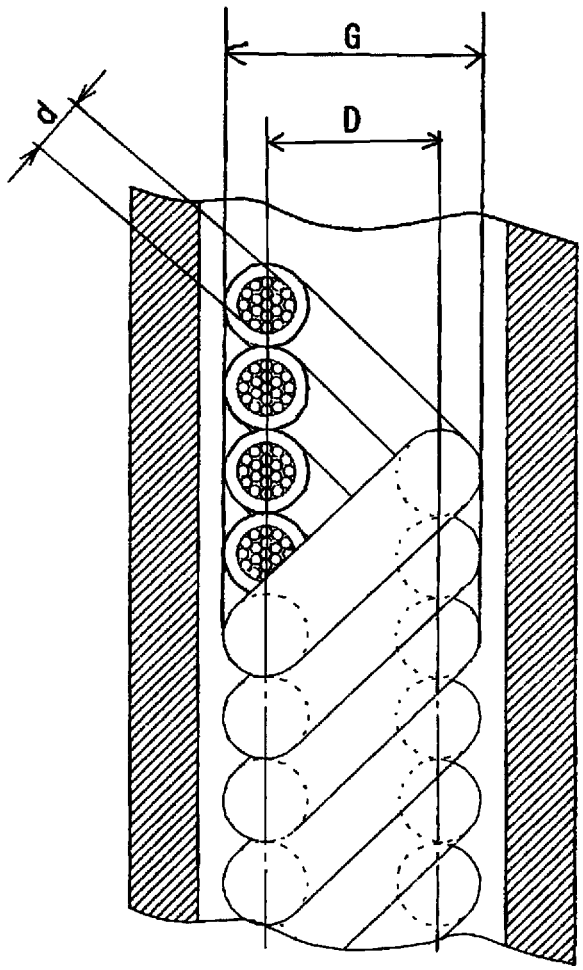
FIG. 3A is a plan view illustrating Example 2 of a coiled cable according to the embodiment of the present invention when seen from the direction orthogonal to the axis thereof.
Figure 3B:
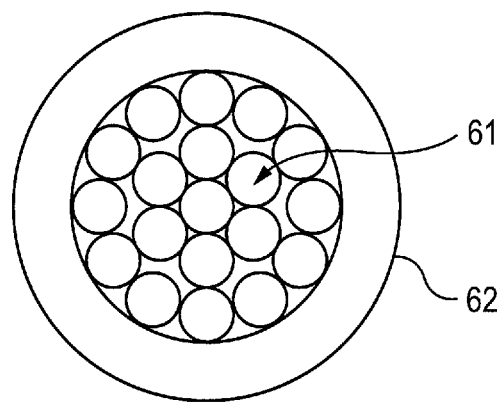
FIG. 3B is an enlarged view illustrating conductor base lines when seen from the axis direction.

A coiled cable 10B of Example 2 is illustrated in FIGS. 3A and 3B. The coiled cable 10B was a simple wire type (19/0.03) of so-called AWG36, and had a dimensional structure with which a spring index (D/d) of the conductor coil of 4.00 was achieved in FIG. 3A.

A conductor 61 was configured by twisting nineteen tin-plated and tin-containing copper alloy wires having an outer diameter of 0.03 mm. Further, an insulator layer 62 was formed by covering the conductor 61 with a PFA to have an outer diameter of 0.22 mm. In addition, four of the above-described cables were tightly wound to have a coil shape, a heat treatment was performed thereon for heat-setting, and the final outer diameter G was φ0.82 mm.

Example 3

Figure 4A:
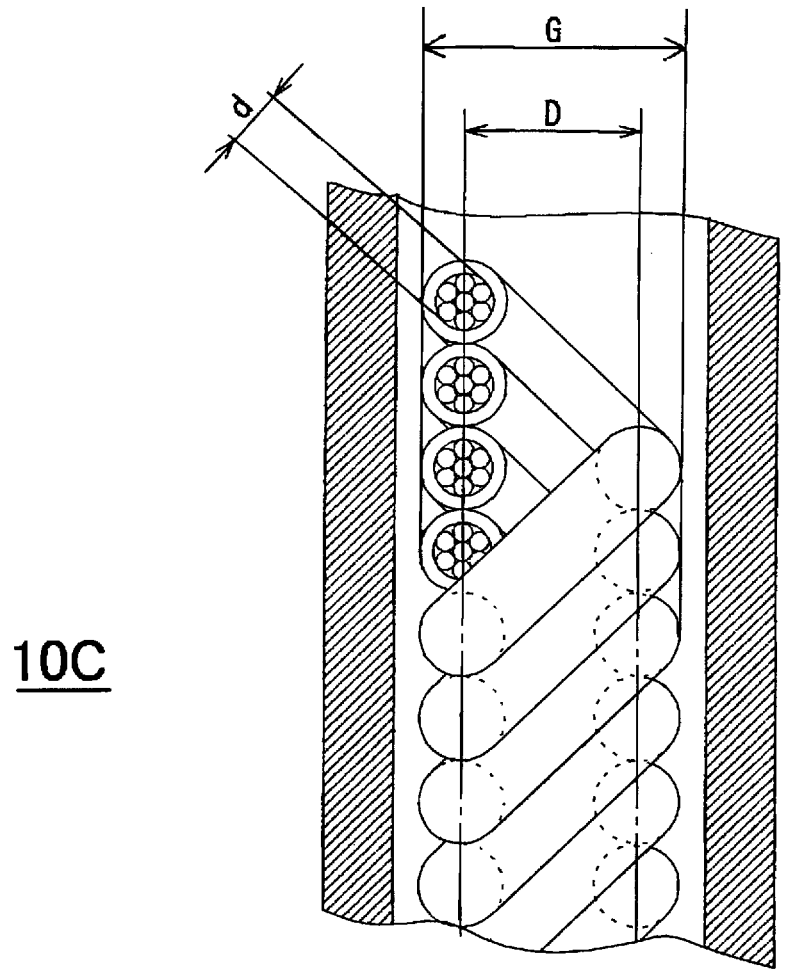
FIG. 4A is a plan view illustrating Example 3 of a coiled cable according to the embodiment of the present invention when seen from the direction orthogonal to the axis thereof.
Figure 4B:
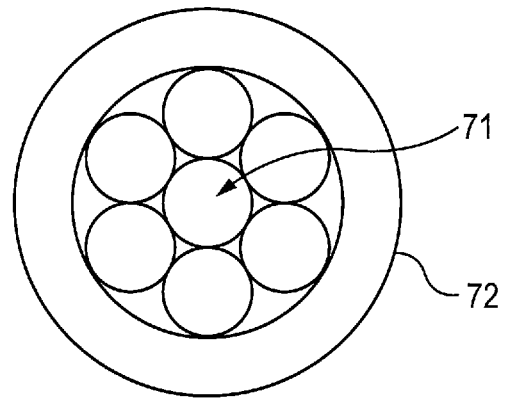
FIG. 4B is an enlarged view illustrating conductor base lines when seen from the axis direction.

A coiled cable 10C of Example 3 is illustrated in FIGS. 4A and 4B. The coiled cable 10C was a simple wire type (7/0.05) of so-called AWG36, and had a dimensional structure with which a spring index (D/d) of the conductor coil of 4.00 was achieved in FIG. 4A.

A conductor 71 was configured by twisting seven tin-plated and tin-containing copper alloy wires having an outer diameter of 0.05 mm. Further, an insulator layer 72 was formed by covering the conductor 71 with a PFA to have an outer diameter of 0.22 mm. In addition, four of the above-described cables were tightly wound to have a coil shape, a heat treatment was performed thereon for heat-setting, and the final outer diameter G was φ0.82 mm.

Comparative Example 1

A coiled cable of Comparative Example 1 (not illustrated) was a simple wire type (1/0.127) of so-called AWG36, and had a dimensional structure with which a spring index (D/d) of 4.72 was achieved. Tin-plated and tin-containing copper alloy wires having an outer diameter of 0.127 mm were used for a conductor, but the tin-plated and tin-containing copper alloy wires were not twisted with each other, which is different from Examples of the present invention described above. An insulator layer was set by covering the conductor with a PFA to have an outer diameter of 0.22 mm. In addition, four of the above-described cables were tightly wound to have a coil shape, a heat treatment was performed for heat-setting, and the final outer diameter G was φ0.82 mm.

Comparative Example 2

A coiled cable of Comparative Example 2 (not illustrated) was a simple wire type (1/0.14) of so-called AWG35, and had a dimensional structure with which a spring index (D/d) of 4.29 was achieved. Tin-plated and tin-containing copper alloy wires having an outer diameter of 0.14 mm were used for a conductor, but the tin-plated and tin-containing copper alloy wires were not twisted with each other, which is different from Examples of the present invention described above. An insulator layer was set by covering the conductor with a PFA to have an outer diameter of 0.22 mm. In addition, four of the above-described cables were tightly wound to have a coil shape, a heat treatment was performed for heat-setting, and the final outer diameter G was φ0.82 mm.

Comparative Example 3

A coiled cable of Comparative Example 3 (not illustrated) was a simple wire type (1/0.16) of so-called AWG34, and had a dimensional structure with which a spring index (D/d) of 3.75 is achieved. Tin-plated and tin-containing copper alloy wires having an outer diameter of 0.16 mm were used for a conductor, but the tin-plated and tin-containing copper alloy wires were not twisted with each other, which is different from Examples of the present invention described above. An insulator layer was set by covering the conductor with a PFA to have an outer diameter of 0.22 mm. In addition, four of the above-described cables were tightly wound to have a coil shape, a heat treatment was performed for heat-setting, and the final outer diameter G was φ0.82 mm.

Three samples for each of Examples 1 to 3 and Comparative Examples 1 to 3 above were prepared, and the number of time of bending until disconnection was examined by setting the samples on bending machine (not illustrated) in which a load of 10 gf of a urethane sheath having 0.1 T was applied and alternate bending test with a bending angle of ±90° at bending R of 2 was performed. The number of times of bending was set to be the average of the three samples. In Examples 1 to 3 and Comparative Examples 1 to 3, values of D (the average diameter of the coil), d (the diameter of the conductor base lines), and D/d (the spring index of a conductor coil) respectively described above are listed in Table 1. In addition, the results of the above-described bending test are listed in Table 2.

TABLE 1

|  | Example 1 | Example 2 | Example 3 | Comparative Example 1 | Comparative Example 2 | Comparative Example 3 |
| --- | --- | --- | --- | --- | --- | --- |
| D | 0.6 | 0.6 | 0.6 | 0.6 | 0.6 | 0.6 |
| d | 0.167 | 0.15 | 0.15 | 0.127 | 0.14 | 0.16 |
| D/d | 3.59 | 4.00 | 4.00 | 4.72 | 4.29 | 3.75 |

TABLE 2

|  | Example 1 | Example 2 | Example 3 | Comparative Example 1 | Comparative Example 2 | Comparative Example 3 |
| --- | --- | --- | --- | --- | --- | --- |
| Number of times at disconnection | 500,000 or greater | 600,000 or greater | 400,000 or greater | 39,144 | 32,432 | 21,726 |

In Table 2, values corresponding to respective Examples and Comparative Examples are average values of three samples with respect to the numbers of times of bending until disconnection. In Table 1, while disconnection occurred with the numbers of times of bending in the range of approximately 20,000 to less than 40,000 in Comparative Examples 1 to 3, disconnection did not occur even with the numbers of times of bending of 500,000 or greater, 600,000 or greater, and 400,000 or greater in Examples 1 to 3. That is, it is understood that the samples in Examples withstood the number of times of bending performed approximately 10 times to 30 times as compared with Comparative Examples.

Here, as listed in Table 1, in the respective cables of Examples and Comparative Examples, the spring indices of all conductor coils of Examples 1 to 3 and Comparative Example 3 are 4 or less. The reason that the cable of Comparative Example 3 was disconnected with the number of times of bending smaller than those in the tests of Comparative Examples 1 and 2 is that the torsional stress of the conductor is large because the spring index D/d of the conductor coil is 3.75, which is small. However, in Example 1, although the spring index D/d of the conductor coil is 3.59 which is smaller than that of Comparative Example 3, the cable was not disconnected and withstood bending performed 500,000 times or greater. This is because the conductor base lines are made into a coiled cable configured by twisting a plurality of tough pitch coppers, oxygen-free coppers, or copper alloy wires, whose diameters are φ0.008 to φ0.05 in Example 1. Even in Examples 2 and 3, although the spring indices D/d of the conductor coils are 4.00 which is smaller than those of Comparative Examples 1 (D/d=4.72) and 2 (D/d=4.29), the cable was not disconnected and withstood bending performed 600,000 times or greater and 400,000 times or greater, respectively. This is also because the conductor base lines are made into coiled cables configured by twisting a plurality of tough pitch coppers, oxygen-free coppers, or copper alloy wires, whose diameters are φ0.008 to φ0.05 in Examples 2 and 3.

In this manner, in the coiled cables of Examples 1 to 3, since the outer diameters are relatively small due to the dimensional structures with which spring indices (D/d) of the conductor coils are in the range of 2≤D/d≤4, coiled cables which are light in weight can be prepared, and since the conductor base lines are configured by twisting a plurality of tough pitch coppers, oxygen-free coppers, or copper alloy wires, whose diameters are φ0.008 to φ0.05, coiled cables which are highly excellent in durability can be obtained. Further, since excellent bending durability can be obtained, the cable has flexibility even in a case of being slightly bent, so that the mechanical stress on a living body can be reduced when the cable is used in the living body.

In addition, measurement results of spring constants of respective Examples 1 to 3 and Comparative Examples 1 to 3 are listed in Table 3.

TABLE 3

|  | Example 1 | Example 2 | Example 3 | Comparative Example 1 | Comparative Example 2 | Comparative Example 3 |
|---|---|---|---|---|---|---|
| Spring constant (gf/mm) | 2.0 | 4.2 | 6.3 | 20.0 | 33.3 | 50.0 |

The spring constants of Table 3 were obtained, with respect to coiled cables respectively having a coil length of 100 mm, by suspending a weight having a load of 50 gf and measuring the extended length (mm) of a mark which is marked at 100 mm. The spring constant is represented by a relationship of "Spring Constant=50 gf/extended length (mm)."

Next, as to coiled cables whose spring indices (D/d) described above were 2, 3, 4, 5, 6, 7, and 8 which were different from one another in the range of 2 to 8, a relationship between respective spring indices (D/d) and increase rate of conductor resistance (%) was calculated using coiled cables respectively having a diameter (d) of 0.22, and the relationship was examined. The respective calculated values are listed in Table 4.

TABLE 4

| D/d | 2 | 3 | 4 | 5 | 6 | 7 | 8 |
|---|---|---|---|---|---|---|---|
| Increase rate (%) | 47 | 121 | 194 | 267 | 339 | 414 | 485 |

Figure 5:
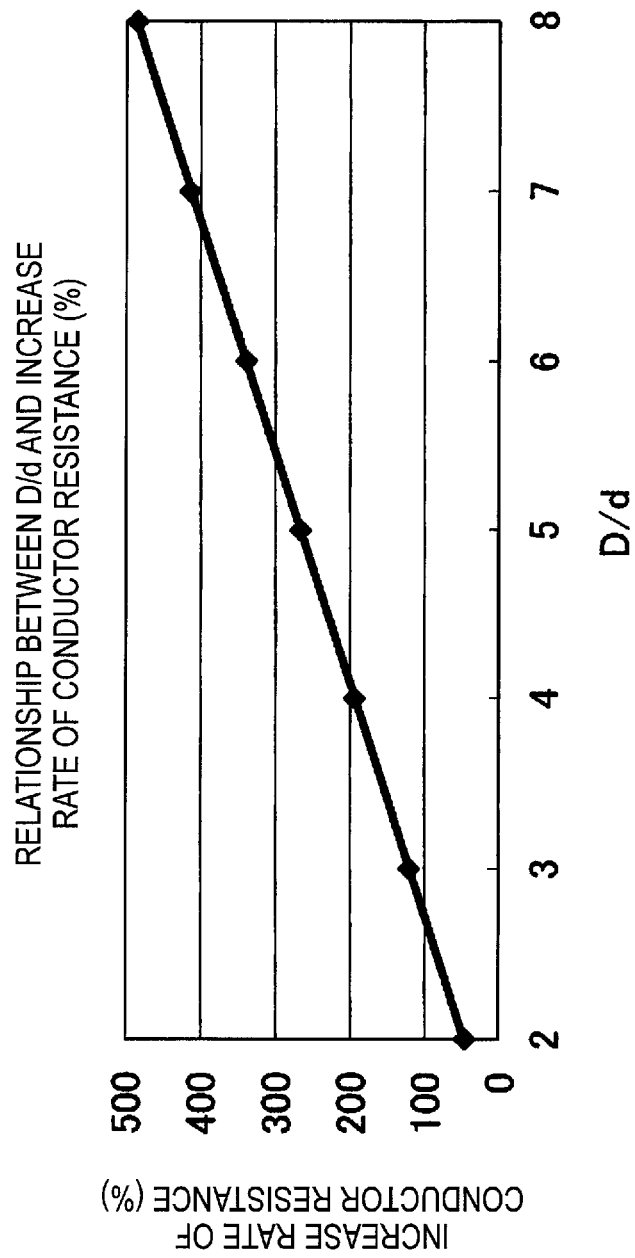
FIG. 5 is a graph illustrating a relationship between a spring index (D/d) and an increase rate (%) of conductor resistance of a conductor coil.

FIG. 5 is a graph illustrating a relationship between the spring index (D/d) of the conductor coil and the increase rate (%) of conductor resistance in the calculated values of Table 4. As understood from Table 4, in the coiled cables whose spring indices (D/d) described above are 2, 3, and 4, the increase rates of conductor resistance are 47, 121, and 194 (%), respectively. These values of the increase rates of conductor resistance are less than 200% as compared with the coiled cables whose spring indices (D/d) of the conductor coil are 5, 6, 7, and 8. As understood from the graph of FIG. 5, when the spring index (D/d) of the conductor coil is greater than 4, the increase rate of conductor resistance exceeds 200 (%). In this manner, it was possible to confirm that the coiled cable 10 with low conductor resistance can be prepared by adjusting the spring index (D/d) of the conductor coil to be within the range of 2≤D/d≤4.

The above-described test results and calculation results are considered in detail. The spring index (D/d) was necessary to be greater than or equal to 7.8 in order to obtain a remarkable effect of reducing an internal stress in examples in the related art described in, for example, Patent Document 1. This effect is noted as "reducing internal stress," and the internal stress indicates a compression stress applied to an inner ring side of a conductor at the time of bending and a tensile stress applied to an outer ring side thereof.

It is understood that since a conductor ($\phi$0.127 from the figure: AWG36 wires, similar to those of Examples) such as DFT (Drawn Filled Tubing) or DBS (Drawn Brazed Strand) apparently functioning as a simple wire is used, the effect of reducing the internal stress cannot be sufficiently obtained unless the spring index (D/d) is large.

In the present invention, for reducing the internal stress, a plurality of materials having a small wire diameter ($\phi$0.008 to $\phi$0.05) are twisted with each other without large spring index (D/d) thereof. Since the bending stress with respect to the same bending R becomes larger in proportion to the fourth power of wire diameter, the present invention uses the fact that the internal stress can be reduced using a small wire diameter.

Practically, since dispersion of the stress is present in the torsion direction or the like, results may not be the same as those described above, but it is certain that the internal stress can be reduced.

In comparison results using the AWG36 wires having the same cross-sectional areas as in Examples, it was confirmed that the bending durability in a case where a conductor having a diameter of $\phi$0.05 or less is used is 10 times or greater than the bending durability in a case where a simple wire having a spring index of 1/0.127 is used, and this indicates that the spring index (D/d) of the conductor coil is not necessary to be greater than or equal to 7.8. In this manner, it is possible to adjust the outer diameter of a coil to be significantly small. As a result, the outer diameter of a lead wire becomes small, and QOL improvement of a patient can be achieved by reducing a burden on a patient when the cable is used in a living body. Further, a wiring space can be reduced due to the reduction in diameter when the cable is used for moving parts of a device.

In materials used for winding coils, the required amount of the materials in coils having the same length can be suppressed to be ½ or less by adjusting "D/d=7.8 or greater" to "D/d=4.0 or less." It is possible to decrease the conductor resistance to ½ or less. As a result, the weight can be reduced. Further, since power consumption converted to heat by the conductor resistance of a lead wire can be suppressed when used for a pacemaker or the like, it is possible to improve the battery life.

In addition, due to the effect of reducing the internal stress by reducing the wire diameter, the spring constant of a coil which is coil-wound in the same manner using an electric wire having the same cross-sectional area of a conductor and the same outer diameter is decreased to ⅓ or less in a test. In a coaxial cable whose wire diameter is smaller, the above-described effect appears more significantly; and a test result of the spring constant becoming 1/10 is obtained.

When the spring constant is small, it is known that this appears as flexibility of a coil in the longitudinal direction. When a coil is flexible, an effect of reducing a burden at the time of operation becomes great and remarkable effects of greatly helping reduction of a burden on a patient and prevention of discomfort in a case of a pacemaker or the like can be obtained.

Moreover, in the above-described embodiment, the four conductor base lines of the coiled cable 10 were arranged in parallel, but one conductor base line may be wound to form a coil shape or two to eight conductor base lines may be wound to form a coil shape by being arranged in parallel. Further, the number of materials to be twisted is not particularly limited as long as respective conductor base lines are configured by twisting a plurality of conductor materials having a diameter of $\phi$0.008 to $\phi$0.05.

INDUSTRIAL APPLICABILITY

Since the coiled electric wire of the present invention is extremely thin, the coiled electric wire can be applied to a medical field such as an endoscope; a small portable computer; and a small electronic apparatus such as a mobile phone.

REFERENCE SIGNS LIST

10: COILED CABLE
12: CONDUCTOR COIL
16: COVERING LAYER
21 to 24: CONDUCTOR BASE LINES
42: INSULATION COATING LAYER

The invention claimed is:

1. A coiled cable comprising a conductor coil formed by winding 1 to 8 conductor base lines having a diameter (d), to each of which an insulation coating layer is applied, into a coil shape having a coil average diameter (D),
wherein the conductor coil is set to have a spring index (D/d) satisfying a relationship of $2 \leq D/d \leq 4$, and
the conductor base lines are configured by twisting a plurality of conductor materials having a diameter of $\phi 0.008$ to $\phi 0.05$.

2. The coiled cable according to claim 1, wherein the conductor base lines are electric wires which include a plurality of conductors and an insulator layer.

3. The coiled cable according to claim 1, wherein the conductor base lines are coaxial cables which include an inner conductor, a dielectric layer, an outer conductor layer, and a protective coating layer.

4. The coiled cable according to claim 1, wherein the insulation coating layer includes a fluorine resin including one or two or more materials selected from an ethylene-tetrafluoroethylene copolymer (ETFE), a tetrafluoroethylene-hexafluoropropylene copolymer (FEP), a perfluoroalkyl vinyl ether copolymer resin (PFA), and polytetrafluoroethylene (PTFE).

5. The coiled cable according to claim 4, wherein the conductor base lines are electric wires which include a plurality of conductors and an insulator layer, or coaxial cables which include an inner conductor, a dielectric layer, an outer conductor layer, and a protective coating layer.

6. The coiled cable according to claim 1, further comprising a resin layer having a stretch property and having a shore A hardness of 90 or less as a covering layer which covers an inner peripheral surface or an outer peripheral surface of the conductor coil.

7. The coiled cable according to claim 6, wherein the conductor base lines are electric wires which include a plurality of conductors and an insulator layer, or coaxial cables which include an inner conductor, a dielectric layer, an outer conductor layer, and a protective coating layer.

8. The coiled cable according to claim 7, wherein the insulation coating layer includes a fluorine resin including one or two or more materials selected from an ethylene-tetrafluoroethylene copolymer (ETFE), a tetrafluoroethylene-hexafluoropropylene copolymer (FEP), a perfluoroalkyl vinyl ether copolymer resin (PFA), and polytetrafluoroethylene (PTFE).

9. The coiled cable according to claim 6, wherein the insulation coating layer includes a fluorine resin including one or two or more materials selected from an ethylene-tetrafluoroethylene copolymer (ETFE), a tetrafluoroethylene-hexafluoropropylene copolymer (FEP), a perfluoroalkyl vinyl ether copolymer resin (PFA), and polytetrafluoroethylene (PTFE).

\* \* \* \* \*